United States Patent
Sheehan

(10) Patent No.: US 10,639,216 B2
(45) Date of Patent: *May 5, 2020

(54) WEARABLE ABSORBENT ARTICLE WITH ROBUST-FEELING WAISTBAND STRUCTURE

(71) Applicant: The Procter & Gamble Company, Cincinnati, OH (US)

(72) Inventor: Astrid Annette Sheehan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 365 days.

This patent is subject to a terminal disclaimer.

(21) Appl. No.: 15/705,360

(22) Filed: Sep. 15, 2017

(65) Prior Publication Data

US 2018/0000664 A1    Jan. 4, 2018

Related U.S. Application Data

(63) Continuation of application No. 13/928,493, filed on Jun. 27, 2013, now Pat. No. 9,820,896.

(51) Int. Cl.
*A61F 13/15* (2006.01)
*A61F 13/532* (2006.01)
(Continued)

(52) U.S. Cl.
CPC .... *A61F 13/5323* (2013.01); *A61F 13/15203* (2013.01); *A61F 13/496* (2013.01);
(Continued)

(58) Field of Classification Search
CPC ............ A61F 13/5323; A61F 13/15203; A61F 13/49011; A61F 13/496; A61F 13/5638;
(Continued)

(56) References Cited

U.S. PATENT DOCUMENTS 4,610,678 A    9/1986    Wiesman et al.
4,673,402 A    6/1987    Weisman et al.
(Continued)

FOREIGN PATENT DOCUMENTS

GB    2216774    10/1989
WO    WO 96-21408 A2    7/1996

OTHER PUBLICATIONS

PCT International Search Report dated Oct. 17, 2014 (11 pages).
All Office Actions, U.S. Appl. No. 13/928,493.

*Primary Examiner* — Jacqueline F Stephens
(74) *Attorney, Agent, or Firm* — Christian M. Best; William E. Gallagher

(57) ABSTRACT

A disposable diaper having front and rear augmented waistband zones having a specified size and stiffness is disclosed. For relatively thinner, less bulky diapers of currently marketed designs, providing augmented waistband zones is believed to reduce mental and physical effort for the caregiver in application of the diaper. The augmented waistband zones provide a robust-feeling structure proximate the waist edges, which the caregiver may grasp at front and rear to adjust the diaper on the wearer. Caregiver perception of a need to reach deeper into the diaper structure to grasp it at a thicker area to tug at it is believed to be reduced.

14 Claims, 4 Drawing Sheets

(51) Int. Cl.
*A61L 15/22* (2006.01)
*A61F 13/56* (2006.01)
*A61F 13/49* (2006.01)
*A61F 13/496* (2006.01)
*A61F 13/84* (2006.01)
*A61F 13/514* (2006.01)

(52) U.S. Cl.
CPC .... *A61F 13/49011* (2013.01); *A61F 13/5638* (2013.01); *A61F 13/84* (2013.01); *A61L 15/22* (2013.01); *A61F 13/49009* (2013.01); *A61F 13/49012* (2013.01); *A61F 13/51464* (2013.01); *A61F 2013/15357* (2013.01); *A61F 2013/15373* (2013.01)

(58) Field of Classification Search
CPC ............... A61F 13/84; A61F 13/49009; A61F 13/49012; A61F 13/51464; A61F 2013/15357; A61F 2013/15373; A61L 15/22
USPC .............. 604/385.24, 385.26, 385.29, 385.3, 604/385.31
See application file for complete search history.

(56) References Cited

U.S. PATENT DOCUMENTS

| | | |
|---|---|---|
| 4,834,735 A | 5/1989 | Alemany et al. |
| 4,888,231 A | 12/1989 | Angstadt |
| 5,137,537 A | 8/1992 | Herron et al. |
| 5,147,435 A | 9/1992 | Kubota et al. |
| 5,260,345 A | 11/1993 | DesMarais et al. |
| 5,342,338 A | 8/1994 | Roe |
| 5,387,207 A | 2/1995 | Dyer et al. |
| 5,527,305 A | 6/1996 | Goulait et al. |
| 5,602,109 A | 2/1997 | Masor et al. |
| 5,625,222 A | 4/1997 | Yoneda et al. |
| 5,649,920 A | 7/1997 | LaVon et al. |
| 6,645,569 B2 | 11/2003 | Cramer et al. |
| 6,863,933 B2 | 3/2005 | Cramer et al. |
| 7,112,621 B2 | 9/2006 | Rohrbaugh et al. |
| 7,805,818 B2 | 10/2010 | Horn et al. |
| 7,895,178 B2 | 2/2011 | Skillen et al. |
| 8,017,827 B2 | 9/2011 | Hundorf et al. |
| 8,388,596 B2 | 3/2013 | Horn et al. |
| 8,449,517 B2 | 5/2013 | Ueda et al. |
| 8,454,572 B2 | 6/2013 | Roe et al. |
| 8,496,637 B2 | 7/2013 | Hundorf et al. |
| 8,728,051 B2 | 5/2014 | Lu et al. |
| 9,820,896 B2 * | 11/2017 | Sheehan ............ A61F 13/5323 |
| 2002/0115979 A1 | 8/2002 | Ikeda |
| 2003/0069557 A1 | 4/2003 | Driskell |
| 2003/0148684 A1 | 8/2003 | Cramer et al. |
| 2005/0008839 A1 | 10/2005 | Cramer et al. |
| 2008/0312617 A1 | 12/2008 | Ashton et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312625 A1 | 12/2008 | Hundorf et al. |
| 2008/0312628 A1 | 12/2008 | Hundorf et al. |
| 2011/0092947 A1 | 4/2011 | Kline et al. |
| 2012/0143162 A1 | 6/2012 | Tomoko et al. |
| 2012/0277702 A1 | 11/2012 | Raycheck et al. |
| 2012/0277713 A1 | 11/2012 | Raycheck et al. |
| 2014/0000070 A1 | 1/2014 | Ashraf et al. |
| 2014/0005621 A1 | 1/2014 | Roe et al. |

\* cited by examiner

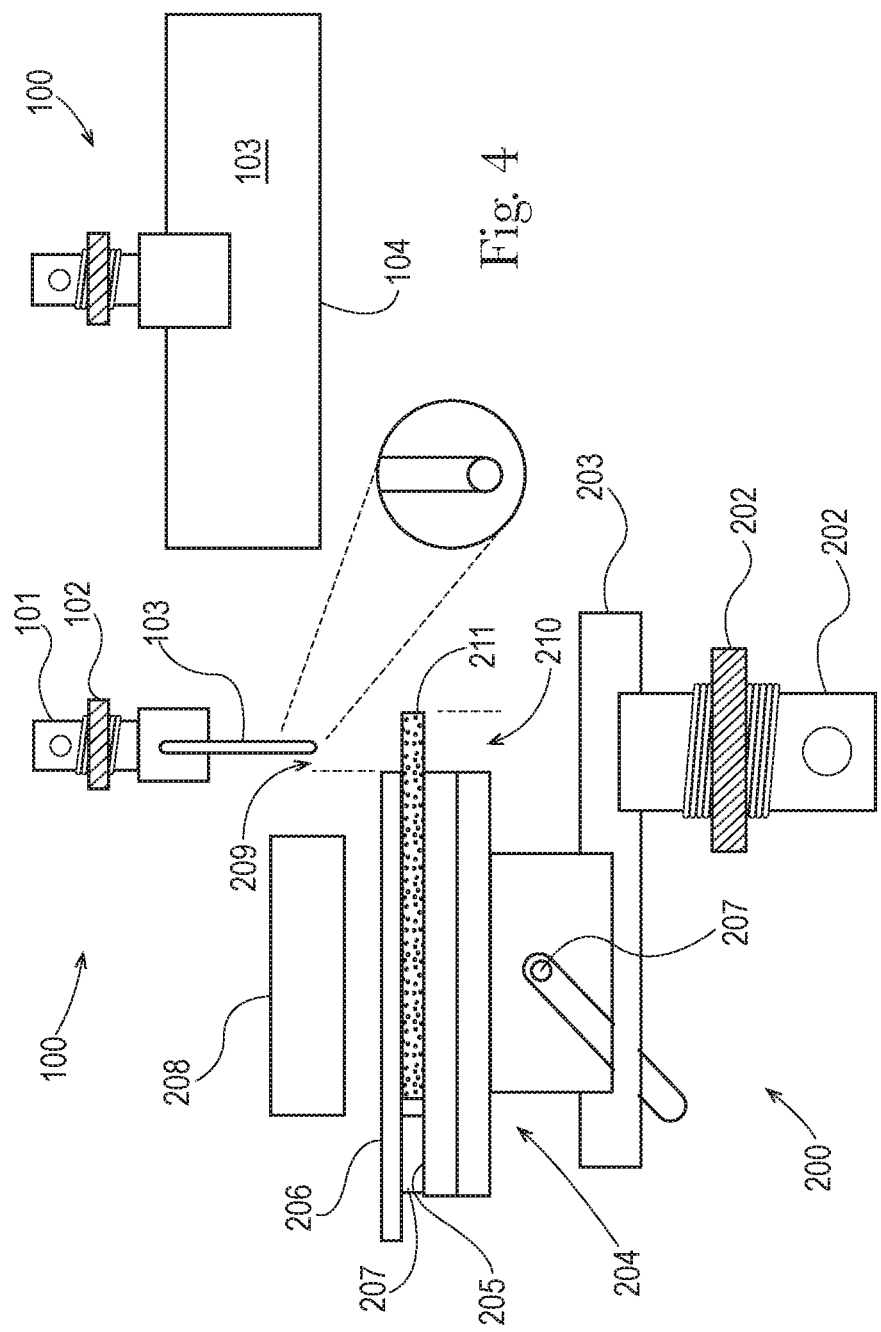

US 10,639,216 B2

WEARABLE ABSORBENT ARTICLE WITH ROBUST-FEELING WAISTBAND STRUCTURE

CROSS REFERENCE TO RELATED APPLICATION

This application is a continuation of application Ser. No. 13/928,493, filed Jun. 27, 2013, the substance of which is incorporated herein by reference.

BACKGROUND

Improvements in manufacturing techniques and developments of material technology have allowed manufacturers of disposable diapers to reduce the quantities of materials used in manufacture and reduce the size, bulk and/or weight of various components of such products. For example, the development and improvement of superabsorbent polymers (also known as absorbent gelling materials), and improvements in absorbent core designs, have enabled manufacturers to reduce the size and bulkiness of absorbent core components. Improvements in polymer materials and processing techniques have enabled manufacturers to use lower basis-weight components including nonwoven web materials and film materials. This has enabled per-unit savings in costs of materials and shipping, without compromising the absorbency or containment functions of the products.

As a result of these improvements, current disposable diaper designs, while relatively light and non-bulky, may also have attributes consciously or unconsciously perceived negatively by some consumers. In some current designs the upper waist regions of the diapers may have relatively few or no absorbency components and may consist only of a few layers of relatively low basis weight, thin web materials. In such current designs the upper waist regions may have an insubstantial, flimsy feel to the consumer.

Caregiver habits and practices relating to applying diapers to children have been observed. It has been observed that, after fastening diapers on children, some caregivers, positioning themselves alongside the child, tend to grasp the diaper between thumb and fingers of their right and left hands, at the front and rear waist regions, in order to tug and adjust the diaper on the child for optimal fit. It has been observed that, with some current diaper designs having relatively thin structures at the upper waist regions, those caregivers may tend to reach down into the diaper with thumb and/or fingers to the absorbent core region, to grasp the diaper at front and rear locations it is believed they perceive to be more structurally robust, to make these final adjustments. It is believed that this practice or habit, subtly but undesirably, contributes to the overall mental and physical effort exerted by the caregiver for the diapering process.

Consequently, a cost-effective way of reducing or eliminating this extra effort and/or the perceived need therefor is desirable.

DESCRIPTION OF THE FIGURES

FIG. 3 is a schematic frontal view of components of fixtures for testing stiffness according to the Stiffness Test Method described herein;

FIG. 4 is a schematic side view of the plunger blade component of the fixtures of FIG. 3;

DESCRIPTION OF EMBODIMENTS

Figure 1:
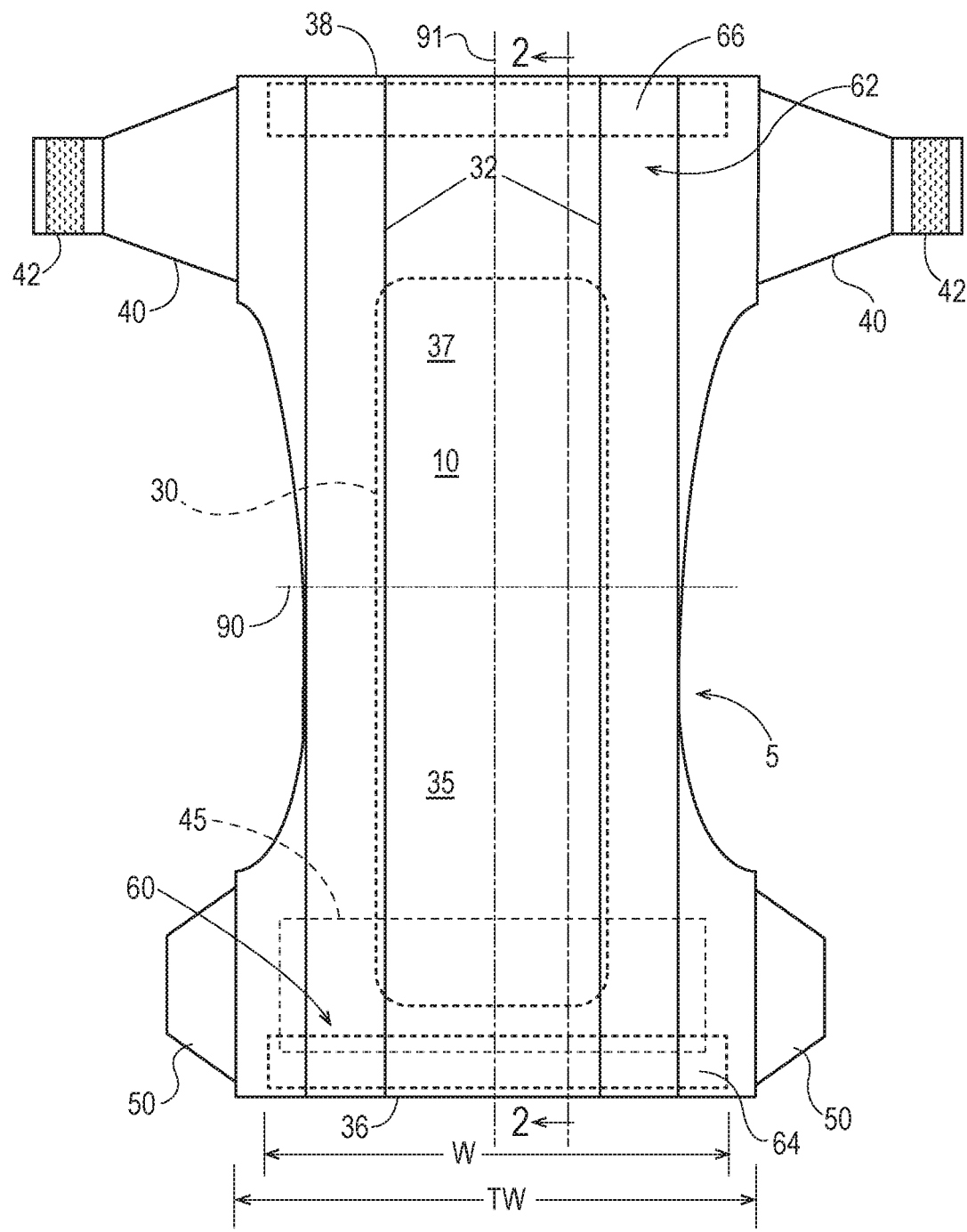
FIG. 1 is a schematic plan view of a disposable diaper laid out extended and flat, with its wearer-facing surfaces facing the viewer.

As used herein, the following terms will have the meanings set forth:

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Caliper" is a measurement of a diaper according to the Caliper Measurement Method set forth herein.

The term "elastic" or "elastomeric" refers to the property of a material that can extend, without substantial rupture or breakage, to a strain of 100% in the Hysteresis Test, with a set less than or equal to 10% of the elongation as measured according to the Hysteresis Test. For example, a material that has an initial length of 25 millimeters and extends 25 millimeters to an extended length of 50 millimeters (100% elongation) with a set of 2 millimeters (8% of the elongation), when subjected to the Hysteresis Test, would be considered elastic.

"Film" means a skin-like or membrane-like material formed of one or more polymers, which does not have a form consisting predominately of a web-like structure of consolidated polymer fibers and/or other fibers.

"Inboard" and "outboard" are terms used to relate location of one feature of a diaper to another feature or location thereof, and relate them to either or both the longitudinal and lateral axes. For example, when a feature A is said to lie longitudinally "outboard" of a feature B, feature A lies farther from (but on the same side of) the lateral axis than feature B. When a feature A is said to lie laterally outboard of a feature B, feature A lies farther from (but on the same side of) the longitudinal axis than feature B. Conversely, when a feature A is said to lie longitudinally "inboard" of a feature B, feature A lies closer to (but on the same side of) the lateral axis than feature B; and when a feature A is said to lie laterally "inboard" of a feature B, feature A lies closer to (but on the same side of) the longitudinal axis than feature B. The intersection of the lateral and longitudinal axes is the inboardmost point on a diaper.

"Lateral," relative to a disposable diaper, refers to a direction perpendicular to the longitudinal axis of the diaper.

"Longitudinal," relative to a disposable diaper, refers to a direction parallel to the longitudinal axis of the diaper.

The "longitudinal axis" of a disposable diaper is a line passing through the midpoints of each of the front and rear waist edges of the diaper chassis.

"Long," "length" and other forms thereof, relative to a disposable diaper, refer to a dimension measured along a direction parallel to the longitudinal axis of the diaper.

A "nonwoven" is a manufactured sheet or web of directionally or randomly oriented fibers which are first formed into a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

"Stiffness" is a property to be measured according to the Stiffness Test Method described below.

"Wide," "width" and other forms thereof, relative to a disposable diaper, refer to a dimension measured along a direction perpendicular to the longitudinal axis of the diaper.

Referring now to the Figures, a disposable diaper chassis 5 may be formed of a liquid permeable topsheet 10 and liquid impermeable backsheet 20 with an absorbent core 30 disposed therebetween. The topsheet 10 and backsheet 20 may be affixed together approximately about their perimeters to envelope the absorbent core 30 and form the chassis 5 structure. The chassis 5 will have a front region 35 lying forward of a lateral axis 90 and ending at front waist edge 36, and a rear region 37 lying rearward of lateral axis 90 and ending at rear waist edge 38. For reference, a longitudinal axis 91 may be defined as a line passing through the midpoints of the waist edges 36, 38, bisecting the diaper width; and the lateral axis 90 may be defined as a line perpendicular to the longitudinal axis and bisecting the diaper length.

The chassis 5 and absorbent core 30 may form the main structure of the diaper with other features added to form a composite diaper structure. While the topsheet 10, the backsheet 20, and the absorbent core 30 may be assembled in a variety of well-known configurations, preferred diaper configurations are described generally in U.S. Pat. Nos. 5,554,145; 5,569,234; and 6,004,306.

The topsheet 10 may be fully or partially elasticized and/or may be foreshortened to create a void space between the topsheet 10 and the absorbent core 30. Exemplary structures including elasticized or foreshortened topsheets are described in more detail in U.S. Pat. Nos. 5,037,416; and 5,269,775.

The backsheet 20 may be joined with the topsheet 10. The backsheet 20 may serve to prevent the exudates absorbed by the absorbent core 30 and contained within the diaper from soiling other external articles that may contact the diaper, such as bed sheets and clothing. The backsheet 20 may be substantially impervious to liquids (e.g., urine) and may be formed of a laminate of a nonwoven web and a thin polymeric film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper while still preventing liquid exudates from passing through the backsheet 20. Exemplary breathable materials may include materials such as woven webs, nonwoven webs, composite materials such as film-coated nonwoven webs, and microporous films such as manufactured by Mitsui Toatsu Co., of Japan under the designation ESPOIR and by EXXON Chemical Co., of Bay City, Tex., under the designation EXXAIRE. Suitable breathable composite materials comprising polymer blends are available from Clopay Corporation, Cincinnati, Ohio under the name HYTREL blend Pl 8-3097. Other examples of such breathable composite materials are described in greater detail in PCT Application No. WO 95/16746. Other breathable backsheets including nonwoven webs and apertured formed films are described in U.S. Pat. No. 5,571,096.

Suitable nonwoven web materials useful for forming the backsheet 20 or a layer thereof may include, but are not limited to, spunbond, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers. A suitable nonwoven web material may also be an SMS material, comprising a spunbonded, a meltblown and a further spunbonded stratum or layer or any other combination of spunbonded and melt-blown layers, such as a SMMS or SSMMS etc. Examples include one or more layers of fibers with diameters below 1 micron (nanofibers and nanofiber layers); examples of these rise in combinations of SMS, SMNS, SSMNS or SMNMS nonwoven webs (where "N" designates a nanofiber layer). In some examples, permanently hydrophilic non-wovens, and in particular, nonwovens with durably hydrophilic coatings may be desirable. Typically, the suitable non-woven is air permeable. Typically the suitable nonwoven is water or liquid permeable, but may also be water impermeable by reason of fiber size and density, and hydrophobicity of the fibers. Water or liquid permeability may be enhanced by treatments to render the fibers hydrophilic.

The nonwoven web of the backsheet may be formed predominately of polymeric fibers. In some examples, suitable non-woven fiber materials may include, but are not limited to polymeric materials such as polyolefins, polyesters, polyamide, or specifically polypropylene (PP), polyethylene (PE), poly-lactic acid (PLA), polyethylene terephthalate (PET) and/or blends thereof. Nonwoven fibers may be formed of, or may include as additives or modifiers, components such as aliphatic polyesters, thermoplastic polysaccharides, or other biopolymers (bio-based or renewable polymers).

The individual fibers may be monocomponent or multi-component. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

Further useful nonwovens, fiber compositions, formations of fibers and nonwovens and related methods are described in U.S. Pat. No. 6,645,569 to Cramer et al., U.S. Pat. No. 6,863,933 to Cramer et al., U.S. Pat. No. 7,112,621 to Rohrbaugh et al.; co-pending U.S patent application Ser. Nos. 10/338,603 and 10/338,610 by Cramer et al., and Ser. No. 13/005,237 by Lu et al., the disclosures of which are incorporated by reference herein.

The diaper may have an absorbent core 30 within the envelope-like structure formed by topsheet 10 and backsheet 20. Absorbent core 30 may comprise any absorbent material which is generally compressible, conformable, non-irritating to the wearer's skin, and capable of absorbing and retaining liquids such as urine and other certain body exudates. Absorbent core 30 may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Absorbent core 30 may include a separate layer of liquid acquisition/distribution material, and a section formed of storage material. Generally, acquisition/distribution material may have comparatively rapid absorption and wicking properties, but also may have limited absorption capacity. Conversely, generally, storage material may have comparatively slower absorption and wicking properties, but also may have greater absorption capacity. Thus, acquisition/distribution material may serve to rapidly absorb and distribute gushes of liquid such as urine, while storage material, having greater absorption capacity, may serve to absorb such liquid from the acquisition/distribution material and store it for the time needed until the insert may be replaced.

Absorbent core 30 may be manufactured in a wide variety of sizes and shapes (e.g., rectangular, hourglass, "T"-shaped, etc.). The configuration and construction of absorbent core 30 may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). Examples of absorbent structures for use as absorbent core 30 may include those described in U.S. Pat. Nos. 4,610,678; 4,673,402; 4,834,735; 4,888,231; 5,137,537; 5,147,345; 5,342,338; 5,260,345; 5,387,207; and 5,625,222.

To reduce the overall size and/or thickness of the absorbent core, and thereby improve wearer comfort and reduce the volume of disposable waste created by a soiled insert, it may be desired to construct an absorbent core using the lowest volumes of core materials possible within performance constraints. Toward this end, examples of suitable materials and constructions for a suitable absorbent core are described in, but are not limited to, copending U.S. applications Ser. Nos. 12/141,122; 12/141,124; 12/141,126; 12/141,128; 12/141,130; 12/141,132; 12/141,134; 12/141,141; 12/141,143; and 12/141,146. These applications generally describe absorbent core constructions that minimize or eliminate the need for and inclusion of airfelt or other forms of cellulose fiber in combination with particles of superabsorbent polymer (hereinafter, "substantially airfelt-free cores"). Airfelt and other cellulose fiber have been used as absorbent fillers in absorbent cores of disposable diapers. Such fiber possesses absorbent properties and imparts some absorption capacity to an absorbent core, but also is included to provide a structural matrix to hold dispersed particles of superabsorbent polymer and/or absorbent gelling material. While inclusion of such particles enhances absorption capacity, keeping such particles suitably dispersed may be important to prevent the particles from "gel-blocking" in use as they swell with absorbed liquid, causing loss of absorption capacity. The inclusion of airfelt or other cellulose fiber as a matrix for superabsorbent particles can serve to reduce or prevent gel-blocking. However, it also imparts bulk to an absorbent core, even before absorption of any liquids.

In accordance with the disclosures in the applications identified immediately above, an absorbent core 30 having a portion that is substantially airfelt-free may be disposed between the topsheet 10 and the backsheet 20. The core 30 may include a layer formed at least in part of a substrate, distributed particles of AGM, and a thermoplastic adhesive composition capturing the distributed AGM particles and adhering to at least portions of the substrate, thereby immobilizing the AGM particles on or proximate to, and relative to, the substrate.

In addition to providing an absorbent core having reduced bulk, the substantially airfelt-free core may generally be more flexible than an absorbent core containing substantial amounts of airfelt or other cellulose fiber. This enhanced flexibility may enable the core and the diaper to better conform about the wearer's body when in use, providing for improved comfort and less bulky appearance of the diaper.

Additionally, by reducing or eliminating airfelt or other cellulosic fiber material, the substantially airfelt-free core reduces the amount of materials consumed in manufacturing, reduces the amount of space (and in some circumstances, weight) per unit which must be packaged and shipped, conserving resources in that regard, and reduces the amount of materials and bulk which must be disposed of in connection with disposing of a used/soiled diaper.

An absorbent core designed and constructed according to the above description can result in an effectively absorbent but relatively non-bulky absorbent structure giving the diaper a Caliper in the rearward portion of the absorbent core, for example, of less than 4.0 mm, less than 3.5 mm, or even less than 3.0 mm, making the diaper substantially less bulky than older products in the market which were typically more bulky. (For purposes herein, the caliper of a diaper is measured using the Caliper Measurement Method set forth below.) Caliper in the rearward portion of the absorbent core may be deemed relevant because it reflects the amount of bulk that is present and visible from the rear when the diaper is worn. Generally, less bulk may be preferred, for purposes of comfort, for purposes of appearance of the diaper when worn, and for purposes of taking up less space in packaging and shipping.

The diaper may include a pair of oppositely-disposed fastening members 40 extending laterally from each of the left and right sides of the chassis 5 in the rear region 37. Fastening members 40 may be formed of an elastically extensible web material, and be elastically extensible in the lateral direction. Examples of suitable elastically extensible fastening members are described in U.S. application Ser. No. 12/904,220. Each of fastening members 40 may have proximate its distal end a mechanical fastener 42. Mechanical fastener 42 may be a strip or patch of a hooks material (exemplified by the hooks component of a VELCRO fastening system), affixed or adhered to the materials forming fastening member 40 on the wearer-facing surfaces thereof.

The diaper may include a landing zone 45 on the outward-facing surface of the front region 35. Landing zone 45 may be formed of a strip or patch of loops material (exemplified by the loops material component of a VELCRO fastening system) adhered to the outward-facing. A variety of materials may serve as suitable loops material i.e., material having looped fibers and/or lengths of fibers at the outer surface with captured ends, which functions to receive and fastenably capture and hold hooks material brought into facing contact therewith. Examples of suitable landing zone material are described in U.S. Pat. Nos. 8,388,596; 7,895, 718; 7,895,178; and 7,805,818; and in U.S. application Ser. No. 13/538,140. Hooks material and landing zone material may be selected for a combination of desirable fastening and holding performance, cost, and ease of handling/processing in manufacture of the diaper. In some examples, however, a nonwoven web material forming the outer layer of the backsheet may be manufactured to have fiber configuration, fiber strength and fiber bonding configuration to make it suitable for receiving, fastenably capturing and holding suitable hooks brought into facing contact therewith, and to have strength sufficient to resist forcible separation from the hooks so as to provide suitable holding strength, such that a separate patch of loops material is not needed to form the landing zone.

The diaper may include a pair of oppositely disposed front ears 50 extending laterally from each of the left and right sides of the chassis 5 in the front region 35. Front ears 50 may simply be extensions of the materials forming the topsheet 10 and/or backsheet 20, or may be formed separately of a web material (such as a nonwoven web material) and bonded and/or adhered to the chassis 5. Front ears 50 may be used by the caregiver to grasp the diaper at the front region while stretching the fastening members 40 and applying the mechanical fasteners 42 to the landing zone 45 to fasten the diaper about a child.

The diaper may include a pair of barrier cuffs 32. Examples of suitable barrier cuff structures are depicted and described in U.S. application Ser. Nos. 13/537,626; 13/457,521; and 13/457/523.

Figure 2:
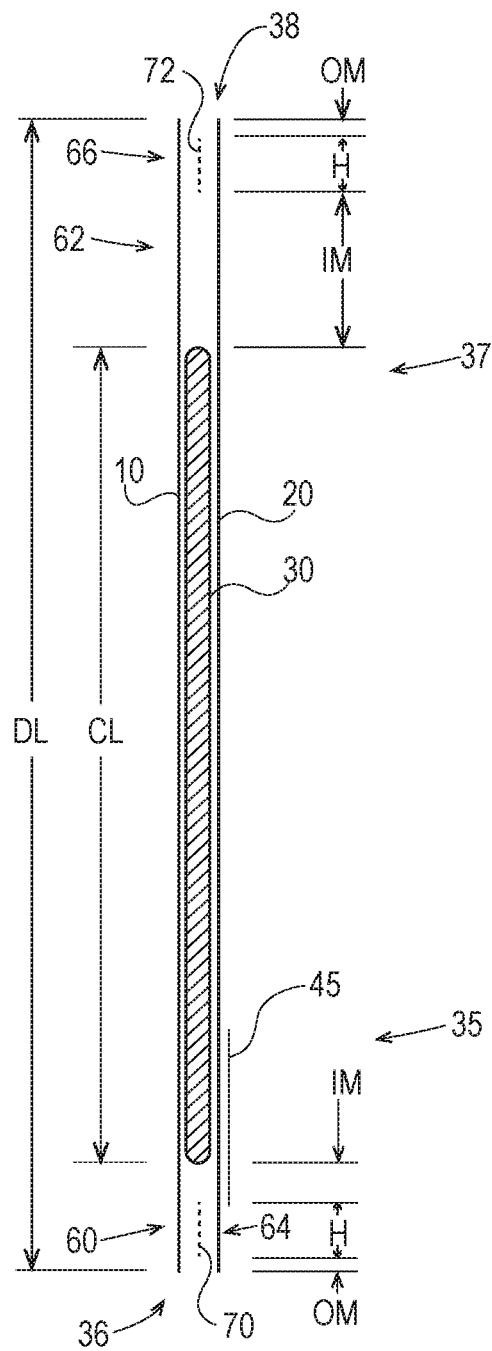
FIG. 2 is a schematic longitudinal cross section of the disposable diaper of FIG. 1, taken through line 2-2 of FIG. 1, and shown schematically with components partially separated for illustration purposes.

As may be appreciated from FIG. 2, front and rear thin portions 60, 62 in the front and rear regions 35, 37 lying immediately longitudinally inward of the waist edges 36, 38, may consist only of a few layers of material, in some cases, as few as two. For example, these thin portions may consist only of the topsheet 10 and backsheet 30; or topsheet 10, backsheet 30 and landing zone 45, with few or no absorbent core components present to add bulk. As noted, this may give a caregiver a perception of insubstantiality or flimsiness of these thin portions. This perception may cause the caregiver to reach down to the absorbent core region to grasp the diaper at perceivably more robust portions of the structure in front and rear to perform fit adjustments by tugging after fastening.

Following observations of caregiver practices, without intending to bound by theory, it is believed that augmenting these thin portions 60, 62 proximate the waist edges, by imparting one or more of greater heft, thickness and/or stiffness to them, causes caregivers to grasp the diaper at these higher locations and forego reaching down to the absorbent core region to perform tugging adjustments after fastening. Without intending to be bound by theory, it is believed that relatively greater heft, thickness and/or stiffness, perceivable through tactile feel, tend to implicitly signal to the caregiver that the diaper structure is sufficiently robust at these areas proximate the waist edges to withstand grasping and tugging. It is believed that, to the caregiver, this signal is consciously or unconsciously interpreted to mean that it is unnecessary to reach down to the core region to grasp a perceivably more robust portion of the structure to grasp and tug at the diaper. Thus, it is believed that such augmentation can reduce the physical and mental effort the caregiver consciously or unconsciously exercises in the application of the diaper to a child.

Depending upon the type and nature of augmentation provided, it may also make the waistband areas more capable of withstanding tugging adjustments of differing types without tearing. Such augmentation may be advantageous for the caregiver during the steps often followed in diaper application and removal: tugging the diaper from the rear region to slide it under a reclining child; tugging at the sides of the diaper from the rear region to wrap it about the child; grasping and holding the diaper in the front region during fastening, and final tugging adjustment; and removal: opening the diaper to remove it with aggressive effort. Augmentation of thin portions may help give the caregiver greater confidence in grasping and manipulating the diaper, removing or preventing any perception that particular care or thought is needed.

Perceivable heft, stiffness and/or robustness may be imparted to augment a zone in various ways. These include adding material or layers of material to the structure. As reflected in the figures, front and rear augmented waistband zones 64, 66 may be provided by including respective front and rear layers of augmenting material 70, 72 in addition to the other layers of material forming the diaper structure including the topsheet, backsheet and landing zone. The augmenting material may be any material that imparts additional stiffness, heft and/or mechanical strength to the structure, localized at the augmented waistband zone. By way of non-limiting example, the augmenting material may be an additional layer of nonwoven web material, an additional layer of film, or even an added quantity of polymeric adhesive. As suggested in FIG. 2, the augmenting material may be disposed between the backsheet 20 and topsheet 30; however, it may also be disposed on the outer surface of the backsheet, or on the inner surface of the topsheet, or at any other location among the layers forming the diaper in the thin portions 60, 62.

Elastomeric materials in the form of elastic films, elastic strips or elastic strands, of the types often used as components in disposable diapers, are generally relatively pliable, flexible and stretchy. These characteristics may make an elastomeric material in one of these forms, in an economically desirable quantity/weight/basis weight, insufficient for use as an augmenting material because it may not be sufficient to add the desired degree of stiffness or suitably perceivable structural robustness. Accordingly, it may be desired that the augumenting material not be solely in the form of an elastomeric film, elastomeric strand or elastomeric strip. If an elastomeric material in such form is included in the structure, it may be desired that it be accompanied by layer of augmenting material that is in addition to such elastomeric material.

Adding augmenting material(s) to a diaper may be counterproductive to controlling costs by minimizing materials usage. For this reason, minimizing usage of augmenting material may be desired. At the same time, certain minimum properties and/or values thereof are believed necessary to provide the desired tactile feel and reduction of caregiver effort. These may be reflected in the planar dimensions of the augmenting material(s) added, in the weight(s) of the augmenting materials added, and in the stiffness imparted to the thin portions 60, 62 by the added augmenting materials.

Accordingly, it may be desired that the layer(s) of augmenting material(s) 70, 72 be substantially laterally centered about the longitudinal axis, as suggested in FIG. 1. It may be desired that one or both the layer(s) of augmenting material(s) have a width W that is at least 60 cm, more preferably at least 80 cm, and still more preferably at least 100 cm. Considered differently, without intending to be bound by theory, it is believed that the minimum width of the augmenting material(s) 70, 72 may be suggested by the total width TW of the waist edges 36, 38. It is believed that this is because the total width of a waist edge may affect the lateral variability of the location at which a caregiver will grasp it: A wider waist edge will effect greater lateral variability, and vice versa. Accordingly, it may be desired that width W of one or both of the layer(s) of augmenting material(s) 70, 72 be at least 30%, more preferably at least 35%, and even more preferably at least 40% of the total width TW of the waist edge(s) 36, 38 proximate thereto. (For purposes herein, the total width TW of a waist edge is measured between the laterally outboardmost longitudinally-oriented edges of the backsheet in the front region 35 or rear region 37 of the diaper proximate the waist edge in question.) In the interest of material cost savings, however, it may be desired that the width W of one or both the layer(s) of augmenting material(s) 70, 72 be less than the total width TW of the proximate waist edge(s) 36, 38, more preferably equal to or less than 75% of TW, and still more preferably equal to or less than 50% of TW.

For the purposes of striking a balance between providing an augmented waistband zone of a height H adapted to be tactilely satisfying for a caregiver, based on the size of a thumb-and-fingers grip, and material cost control, it may be desired that one or both the layer(s) of augmenting material(s) 70, 72 have a height H of 10 mm to 30 mm, more preferably 12 mm to 28 mm, and still more preferably 15 mm to 25 mm.

Although FIG. 1 suggests that layers of augmenting materials and the augmented waistband zones defined thereby be rectangular in shape, this is not necessarily required, as long as sufficient widths and heights of the layers of augmenting materials are present.

In combination with the above-described minimum dimensions, or alternatively, it may be desired that the layer(s) of augmenting material(s) 70, 72 add stiffness to the augmented waistband zones 64, 66 they define. It is believed that, to have the desired effects on caregiver perceptions, the augmented waistband zones should have a stiffness of at least 0.50 N (where stiffness is measured using the Stiffness Test Method set forth below). It is believed, however, that stiffness should not be too great, since an excessively stiff waistband zone may cause discomfort for the wearer. Accordingly, it may be desired that stiffness of an augmented waistband zone not exceed 2.0 N. It may be desired that the stiffness of an augmented waistband zone between from 0.50 N to 2.0 N, more preferably from 0.55 to 1.80 N, and still more preferably from 0.60 N to 1.70 N, or any combination of the upper and lower limits of these ranges.

In still further combination with the above-described features, or alternatively, it may be desired that the layer(s) of augmenting material(s) 70, 72 together make up at least 1.0% of the total weight of the disposable diaper without/before the addition of layers of augmenting materials, more preferably at least 1.5%, and even more preferably 2.0%.

In still further combination with any of the above-described features, it may be desired that one or both of the outward margin(s) OM of thin portions 60, 62 lying longitudinally outboard of the augmented waistband zones be limited, to no more than 5.0 mm, more preferably no more than 2.0 mm, and still more preferably, that one or both of the outward margins OM be zero, i.e., that the longitudinally outboardmost edges of the augmented waistband zones be coextensive and coterminous with the waist edges 36, 38. (For purposes herein, an outward margin OM is measured from the longitudinally outboardmost edge of the augmented waistband zone to the proximate waist edge.) This has the effect of placing the augmented waistband zones as close as possible to the waist edges, minimizing the depth the caregiver must reach into the diaper to grasp and perceive structural robustness.

As noted previously, a purpose of the configurations disclosed herein is to reduce caregiver effort by signaling to the caregiver that it is unnecessary to reach down to the absorbent core region to find a robust portion of the diaper structure to grasp. It may be undesirable, therefore, for either or both the layers of augmenting material(s) to longitudinally overlap the absorbent core. Thus, it may be desirable that one or both the layers of augmenting material(s) 70, 72 not longitudinally overlap, underlay or overlay any substantial deposit of cellulose fibers and/or particles of absorbent gelling material effectively forming a portion of the absorbent structure of absorbent core 30.

The diaper may also include elasticized waistbands (not shown) in either or both the front and rear. In one example, a waistband may be elasticized by the inclusion of one or more laterally-oriented strips or strands of elastomeric material (not shown) (elastic members) sandwiched between the topsheet and backsheet. The strips or stands of elastomeric material may be pre-strained and elongated when applied onto/into the other components of the diaper, such that upon completion of manufacture and relaxation, the elastic members contract laterally and cause the topsheet and backsheet to gather laterally, forming corrugations or gathers of topsheet and backsheet material that accommodate lateral stretch when the diaper is worn.

Figure 5A:
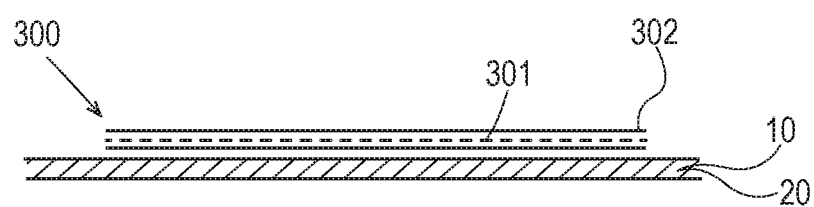
FIGS. 5A and 5B are schematic lateral cross-sectional views of examples of separate elastic waistband structures overlaying a topsheet/backsheet combination.
Figure 5B:
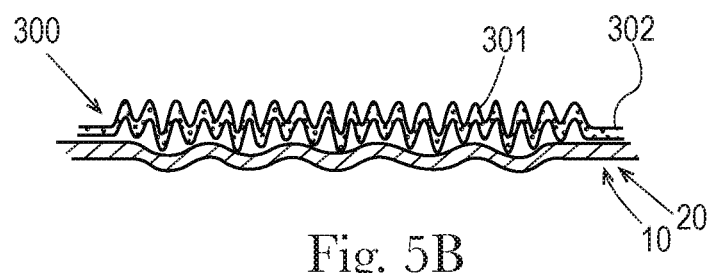

Referring to FIG. 5A, in another example, a separate elastic waistband structure 300 may be applied to the inside of the combined web structure including the topsheet 10 and backsheet 20 in the waistband area, and may be applied to the topsheet on the inside (wearer-facing side) or to the backsheet on the outside. In a particular example, a separate elastic waistband structure may be formed of one or more laterally-oriented elastic members 301 adhered to a laterally-oriented covering strip of nonwoven web material or film material 302, which covers the elastic members. In another particular example, a separate elastic waistband structure 300 may be formed of one or more laterally-oriented elastic members 301 sandwiched and adhered between two laterally-oriented covering strips of nonwoven web material and/or film material 302, which enclose the elastic members to form an elasticized band structure. As suggested in FIG. 5B, a separate elastic waistband structure 300 may be pre-strained and elongated when applied onto the other components of the diaper, such that upon completion of manufacture and relaxation, the elastic members contract laterally and cause the topsheet and backsheet to gather laterally, forming longitudinal corrugations/lateral gathers of topsheet and backsheet material that provide lateral elastic stretch when the diaper is applied and worn. A separate waistband structure may be collocated and/or coextensive with a layer of augmenting material. In a particular example, a separate elastic waistband structure and/or components thereof may serve as the layer of augmenting material for purposes herein. Examples of suitable separate elastic waistband structures are depicted and described in, for example, U.S. patent application Ser. Nos. 13/490,543; 13/490,548; and 13/490,554.

It is believed that providing augmented waistband zones 64, 66 will provide a tactile signal to a caregiver of robustness of the diaper structure at the locations of the zones 64, 66, which they may confidently grasp to tug at the diaper. It is believed, further, that the strength and/or effects of the signal may be enhanced by a visual cue. Thus, it may be desired that one or both of the layers of augmenting material(s) 70, 72 be imparted with a color that visibly contrasts with the color(s) of the immediately surrounding and/or overlying materials. For example, if the backsheet is white or has a white background, a layer of augmenting material overlying or underlying the backsheet (which may be translucent) may be colored, making the associated augmented waistband zone visibly distinct from the immediately surrounding backsheet material. To create a visible contrast, a layer of augmenting material may be colored with a coloring agent (by printing, dyeing, tinting or otherwise) that is not present in or on all of the visible material immediately surrounding the augmenting material in the longitudinal and lateral directions, viewed from the outside of the diaper.

In another alternative, the augmented waistband zone(s) and/or the location thereof may be visually identified, highlighted or visibly demarcated by printing on the underlying or overlying materials. For example, a material of the backsheet may be printed with a block, shape, outline or similar indicium corresponding to and indicating the presence, location and/or shape of the layer of augmenting material, for example, underlying the backsheet.

The following non-limiting examples of combinations of features are contemplated:

1. A disposable diaper, comprising:
    a liquid permeable topsheet forming a wearing-facing surface; a liquid impermeable backsheet forming an outward-facing surface; a front region ending at a front waist edge; a rear region ending at a rear waist edge; an overall length measured from the front waist edge to the rear waist edge; a left and right longitudinal edges connecting the front and rear waist edges; a longitudinal axis dividing the backsheet into left and right halves; elastically extensible left and right fastening members each extending laterally from the respective left and right longitudinal edges in the rear region and each having a mechanical fastener proximate an end thereof; a landing zone in the front region configured to cooperate with the mechanical fasteners to effect attachment therebetween; and an absorbent core disposed between the topsheet and backsheet, the absorbent core having a front core edge, a rear core edge and a core length measured from the front core edge to the rear core edge, the core length being less than the overall length, the absorbent core comprising superabsorbent particles;
    respective front and rear augmented waistband zones in the respective front and rear waist regions, each of the augmented waistband zones being defined by a layer of augmenting material in addition to the topsheet and backsheet, said layer of augmenting material having a top extent, a bottom extent and left and right side extents, a width measured from the left extent to the right extent of at least 60 mm, and substantially centered about the longitudinal axis, and a height measured from the top extent to the bottom extent of at least 10 mm;
    wherein the layer of augmenting material is not solely formed of an elastomeric film, elastomeric strand, or elastomeric strip; and
    wherein both of the front and rear augmented waistband zones has a stiffness of at least 0.50 N.
2. The diaper of combination 1 wherein the top extent of the layer of augmenting material of at least one of the front and rear augmented waistband zones lies within 5 mm of the respective front or rear waist edge.
3. The diaper of combination 2 wherein the top extent of the layer of augmenting material of at least one of the front and rear augmented waistband zones is coextensive with the respective front or rear waist edge.
4. The diaper of any of the preceding combinations wherein the combined weight of the layers of augmenting material of the front and rear augmented waistband zones comprises at least 1.0% of the total weight of the diaper without the layers of augmenting material.
5. The diaper of any of the preceding combinations wherein one or both the layers of augmenting material has a coloring agent therein or thereon, that is not present in or on all of the visible material immediately surrounding the augmenting material in longitudinal and lateral directions, viewed from the outside of the diaper.
6. A disposable diaper, comprising:
    a liquid permeable topsheet forming a wearing-facing surface; a liquid impermeable backsheet forming an outward-facing surface; a front region ending at a front waist edge; a rear region ending at a rear waist edge; an overall length measured from the front waist edge to the rear waist edge; a left and right longitudinal edges connecting the front and rear waist edges; a longitudinal axis dividing the backsheet into left and right halves; elastically extensible left and right fastening members each extending laterally from the respective left and right longitudinal edges in the rear region and each having a mechanical fastener proximate an end thereof; a landing zone in the front region configured to cooperate with the mechanical fasteners to effect attachment therebetween; and an absorbent core disposed between the topsheet and backsheet, the absorbent core having a front core edge, a rear core edge and a core length measured from the front core edge to the rear core edge, the core length being less than the overall length, the absorbent core comprising superabsorbent particles;
    respective front and rear augmented waistband zones in the respective front and rear waist regions, each of the augmented waistband zones being defined by a layer of augmenting material in addition to the topsheet and backsheet, said layer of augmenting material having a top extent, a bottom extent and left and right side extents, a width measured from the left extent to the right extent that comprises at least 30% of the total width of the nearest of the respective front or rear waist edges, and substantially centered about the longitudinal axis, and a height measured from the top extent to the bottom extent of at least 10 mm;
    wherein the layer of augmenting material is not solely formed of an elastomeric film, elastomeric strand, or elastomeric strip; and
    wherein both of the front and rear augmented waistband zones has a stiffness of at least 0.50 N.
7. The diaper of any of the preceding combinations wherein one or both of the front and rear regions include a separate elastic waistband structure.
8. The diaper of any of the preceding combinations having a Caliper of less than 4.0 mm.

Caliper Measurement Method

For purposes herein "Caliper" measurements are performed using an Ono Sokki digital caliper (GS-503 Linear Gauge Sensor with DG-3610 Digital Gauge, Ono Sokki Co, Japan or equivalent) capable of measuring to the nearest 0.01 mm. The circular foot's diameter is 1.00 cm and the applied pressure is 0.30 psi.

Place the sample article on a lab bench with the wearer-facing surface upward. Using scissors, clip any longitudinally-oriented elastic members in barrier cuffs or about leg edges at approximately one-inch intervals or otherwise as effective to allow the article to lay out substantially flat.

Three Measurement Sites are identified on the sample article as follows:
(1) Laterally centered (i.e., along the longitudinal centerline of the diaper) and 5 mm inboard of the rearwardmost edge of the absorbent structure of the absorbent core;
(2) Laterally 20 mm to the left of Measurement Site (1); and
(3) Laterally 20 mm to the right of Measurement Site (1).

For each Measurement Site the caliper is first zeroed by placing the foot directly on the anvil and setting the digital gauge to zero. The foot is then raised and the sample is placed onto the caliper anvil, with the wearer-facing surface upward and the Measurement Site centered under the foot. The foot is lowered at about 5 mm/sec until it rests on the sample. Take a reading after a residence time of 5 seconds, and record to the nearest 0.01 mm. Raise the foot and repeat the measurement in like fashion at the other Measurement Sites. Measurements for the three sites are averaged and reported to the nearest 0.01 mm. A total of 3 substantially identical samples are measured and the measurements for the three Measurement Site on each are averaged and reported to the nearest 0.01 mm.

Stiffness Test Method

Waistband zone stiffness is measured using a constant rate of extension tensile tester with computer interface (a suitable instrument is a MTS Insight Model 1 EL under TestWorks 4 software, as available from MTS Systems Corp., Eden Prairie, Minn.) fitted with a 10 N load cell. A plunger blade 100 shown in FIGS. 3 and 4 is used for the upper movable test fixture and a support platform 200 is used as the lower stationary test fixture. All testing is performed in a conditioned room maintained at 23° C.±2C° and 50%±2% relative humidity.

All dimensional and "left" and "right" references in this test method description are relative the view shown in FIG. 3.

Components of the top fixture 100 are made of a light weight material to maximize the available load cell capacity. The shaft 101 is machined to fit the tensile tester and has a locking collar 102 to stabilize the plunger blade 103 and maintain alignment of its vertical surfaces orthogonal to the test surface 205 of the bottom fixture 200. The plunger blade 103, is 110 mm deep by 35 mm high by 0.9 mm thick, and has a bottom edge 104 rounded with a 0.45 mm radius. The blade is secured to the shaft such that the bottom edge 104 is parallel to the surface of the test surface 205.

The bottom fixture 200 is attached to the tensile tester with the shaft 201 machined to fit the tensile tester and locking collar 202. The laterally movable support platform 204 is mounted on a rail 203 and has a set screw 207 to lock its position after adjustment. The test surface 205 is made from polished stainless steel 90 mm wide by 115 mm deep and is attached to the top of the support platform 204. A cover plate 206 is constructed of 5.6 mm thick Plexiglas that is 140 mm wide by 90 mm deep. A shim piece 207, 5.6 mm thick by 25 mm wide by 90 mm deep, is adhered to the bottom of the cover plate 206 10 mm from, and parallel to, the left edge of the cover plate 206. A 907 g±5 g weight 208 approximately 50 mm wide and 125 mm deep, is rested on the cover-plate during testing, with its left edge aligned with the right edge of the shim 206 as shown in FIG. 3.

Samples are conditioned at 23° C.±2C° and 50%±2% relative humidity for 2 hours prior to testing. The test specimen is removed from the diaper using a cutting die 76.2 mm±1 mm square. The diaper is placed wearer-facing side downward onto a flat-surfaced plate made of LEXAN polycarbonate resin thermoplastic. If the front waist contains elastic, the article is maintained in the relaxed, unstretched state for testing. Measure and mark a site along the longitudinal centerline of the diaper, 74 mm from the front waist edge. Place the die on the top of the article, with the center of the die aligned with the marked site, and with the die's edges parallel and perpendicular to that article's centerline. After alignment a hydraulic press is used to cut the specimen away from the diaper.

Set the gage height such that bottom of the plunger blade 103 is 25.00±0.01 mm above the top plane of the test surface 205. Set the position of the platform 204 such that the left vertical surface of the blade 103 is offset 5.00 mm±0.01 mm to the right of the right side edge of the test surface 205 (distance 209). Program the tensile tester to lower the crosshead downward 35.00 mm at a rate of 127 mm/min while collecting displacement and force data at a rate 100 Hz.

Referring to FIG. 3, place the specimen 211 wearer-facing side downward onto the test surface 205 with the front waist edge of the specimen parallel to the right edge of the test surface 205. Adjust the specimen such that 1.00 cm±0.05 cm of the specimen extends past the right edge of the test surface 205 (distance 210). Place the cover plate 206 over the specimen (the shim will rest on the test surface behind the sample) aligning the right edge of the cover plate 206 with the right edge of the test surface 205. Next, place the weight 208 on top of the cover plate 206, with its left edge aligned with the right edge of the shim 207.

Zero the load cell and the crosshead position. Start the test and collect data. From the resulting force (N) verses displacement curve (mm) calculate the Peak Force (N) and report to the nearest 0.01N. Repeat the test for a total of 15 substantially identical articles. Report the waistband zone stiffness as an average of the 15 replicates, to the nearest 0.01 N.

Hysteresis Test Method

Obtain samples of subject material that have not been activated or otherwise previously substantially stretched. Samples should be sufficient to provide for a gauge length of at least 15 mm along the direction of stretch in the Test, and should be of a constant width (perpendicular to the direction of stretch in the Test) of at least 5 mm.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a) First cycle loading: Pull the sample to the specified strain (herein, 100%) at a constant cross head speed of 100 mm/min. Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min. Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini}) * 100\%$ to the nearest 0.01%.

The testing is repeated for six separate samples and the average and standard deviation reported.

The Hysteresis Test can be suitably modified depending on the expected attributes and/or properties of the particular material sample to be measured. For example, the Test can be suitably modified where a sample of the length and width specified above are not available from the subject pant.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper, comprising:
a liquid permeable topsheet forming a wearing-facing surface; a liquid impermeable backsheet forming an outward-facing surface; a front region ending at a front waist edge; a rear region ending at a rear waist edge; an overall length measured from the front waist edge to the rear waist edge; a left and right longitudinal edges connecting the front and rear waist edges; a longitudinal axis dividing the backsheet into left and right halves; left and right fastening members each extending laterally from the respective left and right longitudinal edges in the rear region and each having a mechanical fastener proximate an end thereof; a landing zone in the front region configured to cooperate with the mechanical fasteners to effect attachment therebetween; and an absorbent core disposed between the topsheet and backsheet, the absorbent core comprising a layer comprising absorbent gelling material and a separate layer of liquid acquisition/distribution material, the absorbent core having a front core edge, a rear core edge and a core length measured from the front core edge to the rear core edge, the core length being less than the overall length, the absorbent core comprising superabsorbent particles;

respective front and rear augmented waistband zones in the respective front and rear waist regions, each of the augmented waistband zones being defined by a layer of augmenting material in addition to the topsheet and backsheet, the layer of augmenting material having a top extent, a bottom extent and left and right side extents, a width measured from the left extent to the right extent of at least 60 mm, and substantially centered about the longitudinal axis, and a height measured from the top extent to the bottom extent of at least 10 mm, the top extent defining an outward margin OM lying longitudinally outboard of the respective front or rear augmented waistband zone, the outward margin OM being no more than 5.0 mm from the respective front waist edge or rear waist edge;

wherein the layer of augmenting material is not solely formed of an elastomeric film, elastomeric strand, or elastomeric strip; and is longitudinally separated and spaced apart from and does not longitudinally overlap the layer of liquid acquisition/distribution material; and wherein both of the front and rear augmented waistband zones has a stiffness of at least 0.50 N.

2. The diaper of claim 1 wherein the top extent of the layer of augmenting material of at least one of the front and rear augmented waistband zones is coextensive with the respective front or rear waist edge.

3. The diaper of claim 1 wherein the combined weight of the layers of augmenting material of the front and rear augmented waistband zones comprises at least 1.0% of the total weight of the diaper without the layers of augmenting material.

4. The diaper of claim 1 wherein one or both the layers of augmenting material has a coloring agent therein or thereon, that is not present in or on all of the visible material immediately surrounding the augmenting material in longitudinal and lateral directions, viewed from the outside of the diaper.

5. The diaper of claim 1 wherein one or both of the front and rear regions include a separate elastic waistband structure.

6. The diaper of claim 1 having a Caliper of less than 4.0 mm.

7. The diaper of claim 1 wherein the left and right fastening members are elastically extensible.

8. A disposable diaper, comprising:
a liquid permeable topsheet forming a wearing-facing surface; a liquid impermeable backsheet forming an outward-facing surface; a front region ending at a front waist edge; a rear region ending at a rear waist edge; an overall length measured from the front waist edge to the rear waist edge; a left and right longitudinal edges connecting the front and rear waist edges; a longitudinal axis dividing the backsheet into left and right halves; left and right fastening members each extending laterally from the respective left and right longitudinal edges in the rear region and each having a mechanical fastener proximate an end thereof; a landing zone in the front region configured to cooperate with the mechanical fasteners to effect attachment therebetween; and an absorbent core disposed between the topsheet and backsheet, the absorbent core comprising a layer comprising absorbent gelling material and a separate layer of liquid acquisition/distribution material, the absorbent core having a front core edge, a rear core edge and a core length measured from the front core edge to the rear core edge, the core length being less than the overall length, the absorbent core comprising superabsorbent particles;
respective front and rear augmented waistband zones in the respective front and rear waist regions, each of the augmented waistband zones being defined by a layer of augmenting material in addition to the topsheet and backsheet, the layer of augmenting material having a top extent, a bottom extent and left and right side extents, a width measured from the left extent to the right extent that comprises at least 30% of the total width of the nearest of the respective front or rear waist edges, and substantially centered about the longitudinal axis, and a height measured from the top extent to the bottom extent of at least 10 mm, the top extent defining an outward margin OM lying longitudinally outboard of the respective front or rear augmented waistband zone, the outward margin OM being no more than 5.0 mm from the respective front waist edge or rear waist edge;
wherein the layer of augmenting material is not solely formed of an elastomeric film, elastomeric strand, or elastomeric strip; and is longitudinally separated and spaced apart from and does not longitudinally overlap the layer of liquid acquisition/distribution material; and
wherein both of the front and rear augmented waistband zones has a stiffness of at least 0.50 N.

9. The diaper of claim 8 wherein one or both of the front and rear regions include a separate elastic waistband structure.

10. The diaper of claim 8 having a Caliper of less than 4.0 mm.

11. The diaper of claim 8 wherein the top extent of the layer of augmenting material of at least one of the front and rear augmented waistband zones is coextensive with the respective front or rear waist edge.

12. The diaper of claim 8 wherein the combined weight of the layers of augmenting material of the front and rear augmented waistband zones comprises at least 1.0% of the total weight of the diaper without the layers of augmenting material.

13. The diaper of claim 8 wherein one or both the layers of augmenting material has a coloring agent therein or thereon, that is not present in or on all of the visible material immediately surrounding the augmenting material in longitudinal and lateral directions, viewed from the outside of the diaper.

14. The diaper of claim 8 wherein the left and right fastening members are elastically extensible.

* * * * *